(12) United States Patent
Kato

(10) Patent No.: US 7,583,385 B2
(45) Date of Patent: *Sep. 1, 2009

(54) OPTICAL TOMOGRAPHY SYSTEM

(75) Inventor: Kiichi Kato, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 76 days.

This patent is subject to a terminal disclaimer.

(21) Appl. No.: 11/529,499

(22) Filed: Sep. 29, 2006

(65) Prior Publication Data

US 2007/0076213 A1    Apr. 5, 2007

(30) Foreign Application Priority Data

Sep. 30, 2005    (JP) .............................. 2005-289124

(51) Int. Cl.
*G01B 9/02*    (2006.01)
(52) U.S. Cl. ..................................... 356/479
(58) Field of Classification Search ................ 356/479, 356/497
See application file for complete search history.

(56) References Cited

U.S. PATENT DOCUMENTS

| 6,552,793 | B1 * | 4/2003 | Kastner ........................ 356/437 |
|---|---|---|---|
| 6,552,796 | B2 | 4/2003 | Magnin et al. |
| 6,636,755 | B2 * | 10/2003 | Toida .......................... 600/407 |
| 7,023,558 | B2 * | 4/2006 | Fee et al. ..................... 356/479 |
| 7,312,879 | B2 * | 12/2007 | Johnston ...................... 356/614 |
| 2004/0090633 | A1 * | 5/2004 | Knuttel ........................ 356/497 |
| 2006/0066865 | A1 * | 3/2006 | Tsujita ........................ 356/479 |
| 2006/0170930 | A1 * | 8/2006 | Li .............................. 356/479 |
| 2006/0264743 | A1 * | 11/2006 | Kleen et al. .................. 600/425 |
| 2007/0019208 | A1 | 1/2007 | Toida |
| 2007/0077045 | A1 * | 4/2007 | Kato ........................... 396/17 |

FOREIGN PATENT DOCUMENTS

JP    2003-172690 A    6/2003

* cited by examiner

*Primary Examiner*—Tarifur Chowdhury
*Assistant Examiner*—Jonathan M Hansen
(74) *Attorney, Agent, or Firm*—Sughrue Mion, PLLC

(57) ABSTRACT

When a tomographic image of an object in a body cavity is to be obtained by an optical coherence tomography measurement employing a probe, the distance between the probe and the object is measured and the optical path length of the measuring light or the reference light is adjusted.

6 Claims, 7 Drawing Sheets

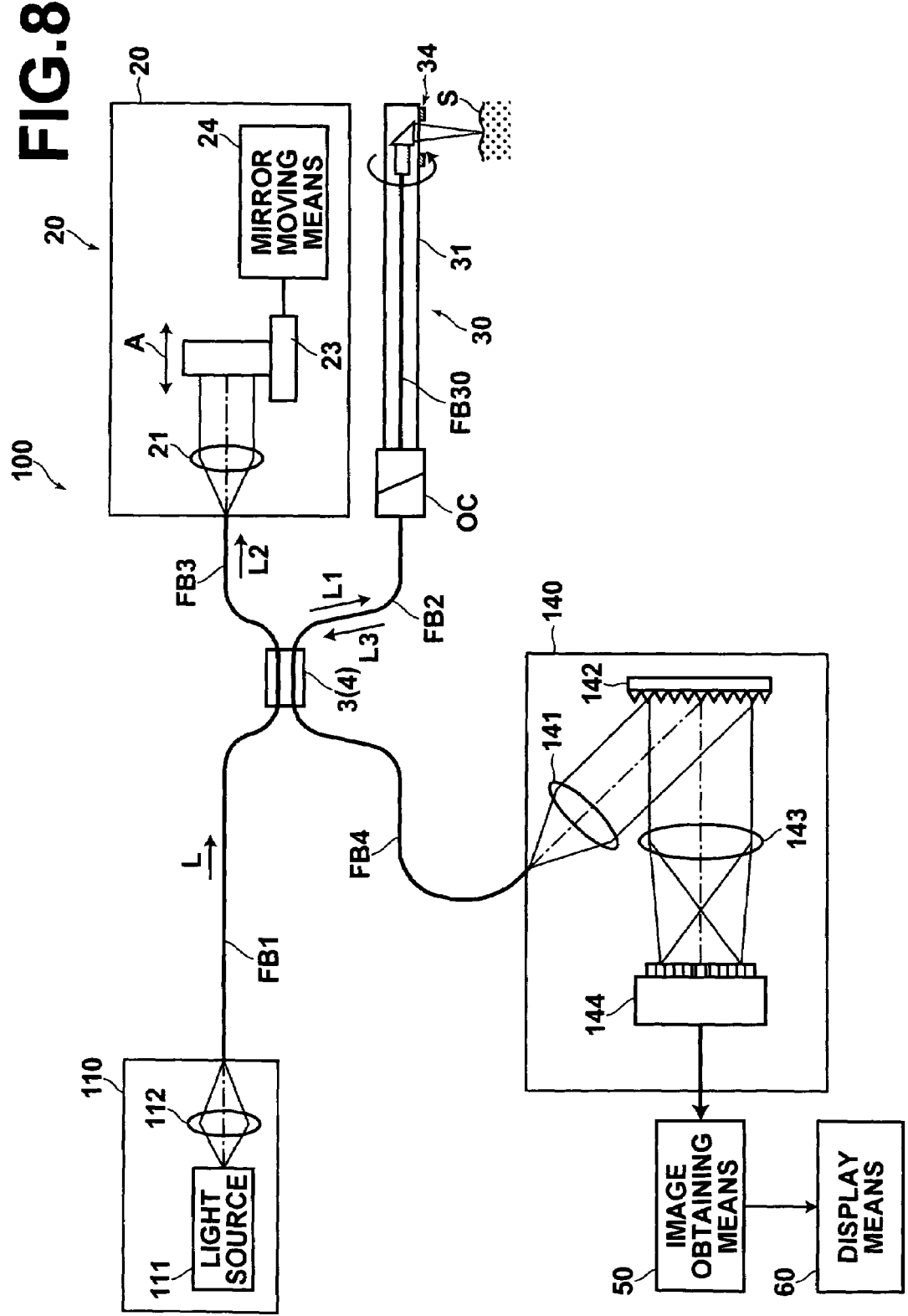

OPTICAL TOMOGRAPHY SYSTEM

BACKGROUND OF THE INVENTION

1. Field of the Invention

This invention relates to an optical tomography system for obtaining an optical tomographic image by measurement of OCT (optical coherence tomography).

2. Description of the Related Art

As a system for obtaining a tomographic image of an object of measurement in a body cavity, there has been known an ultrasonic tomography system. In addition to such an ultrasonic tomography system, there has been proposed an optical tomography system where an optical tomographic image is obtained on the basis of an interference of light by low coherence light. See, for instance, Japanese Unexamined Patent Publication No. 2003-172690. In the system disclosed in Japanese Unexamined Patent Publication No. 2003-172690, an optical tomographic image is obtained by measuring TD-OCT (time domain OCT) and the measuring light is guided into the body cavity by inserting a probe into the body cavity from the forceps port of an endoscope by way of a forceps channel.

More specifically, low coherence light emitted from a light source is divided into measuring light and reference light and the measuring light is projected onto the object of measurement, while the reflected light from the object of measurement is led to a multiplexing means. The reference light is led to the multiplexing means after its optical path length is changed. By the multiplexing means, the reflected light and the reference light are superposed one on another, and interference light due to the superposition is detected by, for instance, heterodyne detection. In the TD-OCT measurement, a phenomenon that interference light is detected when the optical path of the measuring light conforms to the optical path of the reference light in length is used and the measuring position (the depth of measurement) in the object is changed by changing the optical path length of the reference light.

When measuring the OCT by inserting a probe into a body cavity, the probe is mounted on the system body to be demountable since disinfection, cleaning and the like of the probe after use are necessary. That is, a plurality of probes are prepared for one optical tomography system and the probes are changed by the measurement. However there is an individual difference in the length of the optical fiber due to the manufacturing errors and the like, and the optical path length of the measuring light can change each time the probe is changed. Accordingly, in Japanese Unexamined Patent Publication No. 2003-172690, on the basis of the reflected light from the inner surface of a tube (sheath) covering an optical fiber of the probe, the optical path length of the reference light is adjusted to conform to the optical path length of the measuring light.

If the center of rotation of a probe is deviated from the center of a blood vessel when observing a tubular sample such as the blood vessel by rotating the probe, interference light from a part a tomographic image of which is unnecessary prevails to make the measurement inefficient. A method of preventing this has been proposed, for instance, in the U.S. Pat. No. 6,552,796. In the U.S. Pat. No. 6,552,796, the border is recognized from the tomographic images obtained, and the operator manually determines the offset of the center of measurement to store a storage portion a scanning initiating timing according to the amount of offset.

Whereas, as a system for rapidly obtaining a tomographic image without changing the optical path length of the reference light, there has been proposed an SS-OCT (swept source OCT) system where interference light is detected while the frequency of the light emitted from the light source is changed with time. In the SS-OCT system, an interferogram interference intensity signal is obtained without changing the optical path length by sweeping the frequency of the laser beam emitted from the light source to cause the reflected light and the reference light to interfere with each other by the use of a Michelson interferometer. Then a tomographic image is generated by carrying out a Fourier analysis on the interferogram signal in the region of an optical frequency.

Further, as a method of rapidly obtaining a tomographic image without sweeping the optical path length of the reference light, there has been proposed an SD-OCT (spectral domain OCT) measurement, In the SD-OCT measurement, a tomographic image is formed without scanning in the direction of depth, by emitting broad band, low coherence light from a light source by the use of a Michelson interferometer, dividing the low coherence light into measuring light and reference light and carrying out a Fourier analysis on each channeled spectrum signal obtained by decomposing the interference light of the reflected light, which returns when projecting the measuring light onto the object, and the reference light into frequency components.

SUMMARY OF THE INVENTION

Though, in Japanese Unexamined Patent Publication No. 2003-172690 and the U.S. Patent No. 6,552,796, the optical path length is adjusted in order to adjust the individual difference of the probes, it is necessary to adjust the measurement initiating position to position the object to be measured in the range within which it can be measured by the OCT measurement. That is, since the measurable range over which a tomographic image is obtainable by the OCT measurement is limited in the direction of depth, it is necessary to adjust the optical path length of the reference light according to the distance between the probe and the object in order to adjust the measurement initiating position so that the object is positioned in the measurable range.

In the TD-OCT measurement, since the measuring depth is changed by adjusting the optical path length of the reference light, the measurable range can be adjusted by adjusting the optical path length while observing the intensities or the waveforms of the signals obtained by a beat signal measurement or the interferogram measurement of the interference light. However, in the SS-OCT measurement or the SD-OCT measurement, since the reflection information cannot be obtained unless frequency-analysis such as Fourier-transform is carried out on the detected interference light and even when the position of the object is confirmed to adjust the measurement initiating position, frequency-analysis is required, it takes a long time to adjust the measurement initiating position.

In view of the foregoing observations and description, the primary object of the present invention is to provide an optical tomography system in which the adjustment of the measurement initiating position can be carried out in a short time.

In accordance with the present invention, there is provided an optical tomography system for obtaining a tomographic image of an object to be measured comprising a light source unit which emits light, a light dividing means which divides the light emitted from the light source unit into measuring light and reference light, an optical path length adjusting means which adjusts the optical path length of the measuring light or the reference light divided by the light dividing means, a probe having an optical fiber which guides to the object the measuring light divided by the light dividing means and a light emitting portion which emits from an optical fiber the measuring light scanning the object, a multiplexing means which multiplexes the reflected light from the object when the measuring light emitted from the probe is projected onto the object and the reference light, an interference light detecting means which detects interference light of the reflected light and the reference light which have been multiplexed by the multiplexing means, and a tomographic image obtaining means which obtains a tomographic image of the object on the basis of the interference light detected by the interference light detecting means, wherein the improvement comprises that the probe is provided with a distance measuring means which measures the distance to the measuring light projected part onto which the measuring light emitted from the light emitting portion is projected, and the optical path length adjusting means adjusts the optical path length of the measuring light or the reference light by the use of the distance to the object measured by the distance measuring means in order to adjust the position in which a tomographic image signal is to be obtained in synchronization with scanning of the measuring light.

The distance measuring means may be any so long as it can measure the distance to the object. For example, the distance measuring means may comprise a measuring light source which emits distance measuring light toward the object, a photo-sensor which detects the reflected distance measuring light from the object when the distance measuring light is projected onto the object from the measuring light source, and a distance calculating means which calculates the distance to the object from the reflected distance measuring light detected by the photo-sensor.

The tomographic image obtaining means may have a function of correcting the distance between the probe and the measuring light projected part in the tomographic image on the basis of the distance between the probe and the measuring light projected part of the object measured by the distance measuring means when the measuring light is projected onto the object while scanning the object.

The light source unit may emit a laser beam while sweeping the wavelength, while the image obtaining means obtains a tomographic image of the object by carrying out frequency-analysis on the interference light, and the optical path length adjusting means adjusts the optical path length of the measuring light or the reference light in order to adjust the position in which a tomographic image signal is to be obtained.

Further, the light source unit may emit low coherence light while the image obtaining means obtains a tomographic image of the object by carrying out frequency-analysis on the interference light, and the optical path length adjusting means adjusts the optical path length of the measuring light or the reference light in order to adjust the position in which a tomographic image signal is to be obtained.

In accordance with the optical tomography system of the present invention, since a distance measuring means which measures the distance to the measuring light projected part onto which the measuring light emitted from the light emitting portion is projected is provided and the optical path length adjusting means adjusts the optical path length of the measuring light or the reference light by the use of the distance to the object measured by the distance measuring means in order to adjust the position in which a tomographic image signal is to be obtained, the signal processing to detect the measurement initiating position can be eliminated by measuring the distance to the object by the distance measuring means not measuring the distance by the use of the interference light as in obtaining the tomographic images whereby adjustment of the measurement initiating position in the case where, for instance, there are individual differences among the lengths of the probes or the object is in the measurable range can be carried out in a short time when the position in which a tomographic image is to be obtained is set.

Further, when the light emitting portion of the probe projects the measuring light onto the object while scanning the same, and the distance measuring means rotates in synchronization with the light emitting portion, the distance measuring means can measure the distance to the measuring light projected part of the object even if the distance to the measuring light projected part from the light emitting portion of the probe is changed due to rotation of the light emitting portion, whereby the distance to the object can be measured surely and accurately.

When the tomographic image obtaining means has a function of correcting the distance between the probe and the measuring light projected part in the tomographic image on the basis of the distance between the probe and the measuring light projected part of the object measured by the distance measuring means when the measuring light is projected onto the object while rotating, a tomographic image faithfully representing the actual positional relation can be obtained even if the distance between the probe and the measuring light projected part of the object is changed due to rotation of the light emitting portion since the distance between the probe and the measuring light projected part in the tomographic image can be corrected on the basis of the distance between the probe and the measuring light projected part of the object measured by the distance measuring means.

Further, when the light source unit emits a laser beam while sweeping the wavelength or low coherence light while the image obtaining means detects the intensities of the reflected light in positions in the direction of depth of the object and obtains a tomographic image of the object by carrying out frequency-analysis on the interference light, and the optical path length adjusting means adjusts the optical path length of the measuring light or the reference light in order to adjust the position in which a tomographic image signal is to be obtained, the frequency-analysis on the interference light to detect the measurement initiating position becomes unnecessary and the adjustment of the optical path length so that the object is in the measurable range can be carried out in a short time.

BRIEF DESCRIPTION OF THE DRAWINGS

FIG. 8 is a schematic diagram showing an optical tomography system in accordance with a second embodiment of the present invention.

DESCRIPTION OF THE PREFERRED EMBODIMENTS

Figure 1:
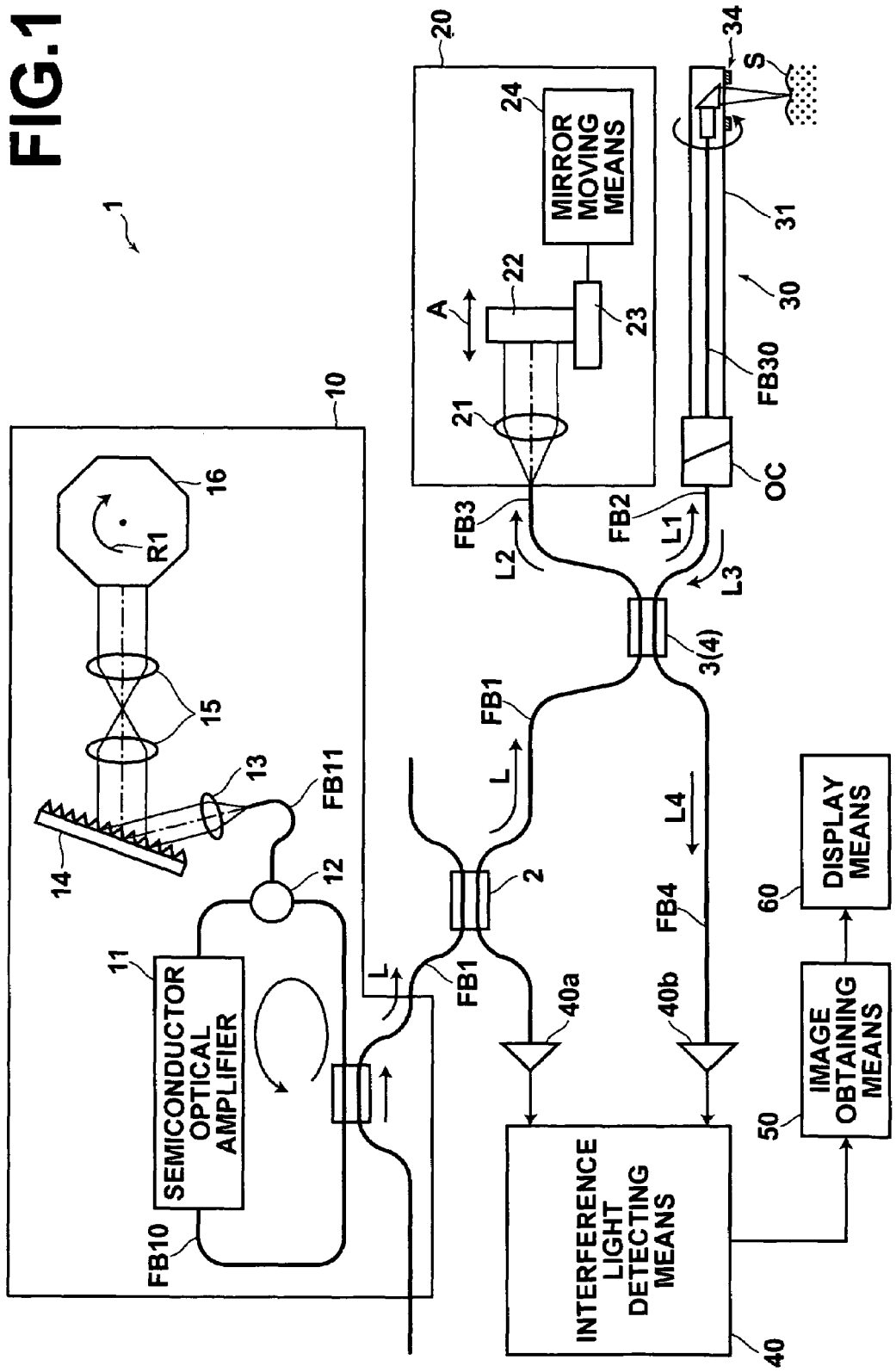
FIG. 1 is a schematic diagram showing an optical tomography system in accordance with a preferred embodiment of the present invention.

Embodiments of the optical tomography system of the present invention will be described in detail with reference to the drawings, hereinbelow. FIG. 1 is a schematic diagram that illustrates an optical tomography system in accordance with a preferred embodiment of the present invention. The optical tomography system 1 of this embodiment is for obtaining a tomographic image of an object of measurement such as a living tissue or a cell in a body cavity by measuring the SS-OCT. The optical tomography system 1 of this embodiment comprises: a light source unit 10 which emits a laser beam L; a light dividing means 3 which divides the laser beam L emitted from the light source unit 10 into measuring light beam L1 and reference light beam L2; an optical path length adjusting means 20 which adjusts the optical path length of the reference light beam L2 divided by the light dividing means; a probe 30 which guides to the object S to be measured the measuring light beam L1 divided by the light dividing means 3; a multiplexing means 4 for multiplexing a reflected light beam L3 from the object S when the measuring light beam L1 is irradiated onto the object S from the probe 30, and the reference light beam L2; an interference light detecting means 40 for detecting interference light beam L4 of the reflected light beam L3 and the reference light beam L2 which have been multiplexed by the multiplexing means 4; and an image obtaining means 50 which detects intensities the measuring light L1 in positions in the direction of depth of the object by carrying out frequency-analysis on the interference light L4 detected by the interference light detecting means 40 and obtains a tomographic image of the object S.

The light source unit 10 emits a laser beam L while sweeping its wavelength and comprises, for instance, a mode synchronized semiconductor laser. Specifically, the light source unit 10 comprises a semiconductor optical amplifier (a semiconductor gain medium) 11 and an optical fiber FB10 connected to the semiconductor optical amplifier 11 at opposite ends thereof. The semiconductor optical amplifier 11 emits weak spontaneous light to one end of the optical fiber FB10 in response to injection of a drive current and amplifies light input from the other end of the optical fiber FB10. When a drive current is supplied to the semiconductor optical amplifier 11, a laser beam L is emitted to the optical fiber FB1 by a loop formed by the semiconductor optical amplifier 11 and the optical fiber FB10.

Further, an optical divider 12 is connected to the optical fiber FB10 and a part of the light beam propagated through the optical fiber FB10 is emitted from the optical divider 12 toward the optical fiber FB11. Light emitted from the optical fiber FB11 travels through the collimator lens 13, the diffraction grating 14 and the optical system 15 and is reflected by the rotating polygon mirror 16. The reflected light is returned to the optical fiber FB11 by way of the optical system 15, the diffraction grating 14 and the collimator lens 13.

The rotating polygon mirror 16 rotates in the direction indicated by arrow R1, to vary the angle of each reflective surface thereof with respect to the optical axis of the optical system 15. Thereby, only a light beam having a specific frequency, from among the light spectrally split by the diffraction grating 14, is returned to the optical fiber FB11.

Figure 2:
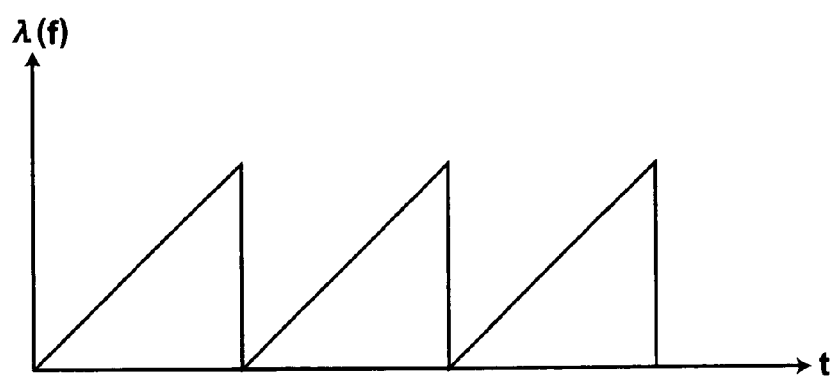
FIG. 2 is a view showing fluctuation in wavelength of the laser beam output from the light source unit of FIG. 1.

The frequency of the light beam that reenters the optical fiber FB11 is determined by the angle formed by the optical axis of the optical system 15 and the reflective surface of the rotating polygon mirror 16. Accordingly, when the rotating polygon mirror 16 rotates in the direction indicated by arrow R1 at a constant speed, the wavelength of the light beam which reenters the optical fiber FB1 is swept at a period as shown in FIG. 2. As a result, a laser beam L which is swept in its wavelength at a period is emitted from the light source unit 10 toward the optical fiber FB1.

The light dividing means 3 of FIG. 1 comprises, for instance, a 2×2 fiber optic coupler and divides the laser beam L led thereto by way of the optical fiber FB1 from the light source unit 10 into the measuring light beam L1 and the reference light beam L2. The light dividing means 3 is optically connected to two optical fibers FB2 and FB3, and the measuring light beam L1 is propagated through the optical fiber FB2 while the reference light beam L2 is propagated through the optical fiber FB3. In FIG. 1, the light dividing means 3 also functions as the multiplexing means 4.

The probe 30 is optically connected to the optical fiber FB2 and the measuring light beam L1 is guided to the probe 30 from the optical fiber FB2. The probe 30 is inserted into a body cavity, for instance, through a forceps port by way of a forceps channel and is removably mounted on the optical fiber FB2 by an optical connector OC.

The optical path length adjusting means 20 is disposed on the side of the optical fiber FB3 radiating the reference light beam L2. The optical path length adjusting means 20 changes the optical path length of the reference light beam L2 in order to adjust the tomographic image obtaining area and comprises an optical system 21 and a reflecting mirror 22. The optical system 21 has a function of making parallel the reference light beam L2 radiated from the optical fiber FB3 and collecting the reference light beam L2 reflected by the reflecting mirror 22 on the optical fiber FB3. The reflecting mirror 22 is disposed on a movable stage 23 which is moved in the direction of arrow A by a mirror moving means 24. In response to movement of the movable stage 23 in the direction of arrow A, the optical path length of the reference light beam L2 is changed.

The multiplexing means 4 comprises a 2×2 fiber optic coupler, and multiplexes the reference light beam L2 which has been changed in its optical path length and shifted in its frequency by the optical path length adjusting means 20 and the reflected light beam L3 from the object S to emit the multiplexed light beam toward an interference light detecting means 40 by way of an optical fiber FB4.

The interference light detecting means 40 detects interference light beam L4 of the reflected light beam L3 and the reference light beam L2 which have been multiplexed by the multiplexing means 4 and the image obtaining means 50 detects the intensities of the reflected light beam L3 in positions in the direction of depth of the object S by carrying out frequency analysis on the interference light beam L4 detected by the interference light detecting means 40 and obtains a tomographic image of the object S. In the embodiment shown in FIG. 1, an optical detector 40a which detects the intensity of the laser light beam L branched from an fiber optic coupler 2 of the optical fiber FB1 and an optical detector 40b which detects the intensity of interference light beam L4 are provided and the interference light detecting means 40 has a function of adjusting the balance of the intensity of the interference light beam L4 on the basis of the output of the optical detector 40a. This function suppresses unevenness in the light intensity by the frequency and permits to obtain a clearer image.

Here, detection of the interference light beam L4 in the interference light detecting means 40 and image generation in the image obtaining means 50 will be described briefly. Note that a detailed description of these two points can be found in M. Takeda, "Optical Frequency Scanning Interference Microscopes", Optical Engineering Contact, Vol. 41, No. 7, pp. 426-432, 2003.

When the measuring light beam L1 is projected onto the object S, the reflected light L3 from each depth of the object S and the reference light L2 interfere with each other with various optical path length difference 1. When the light intensity of the interference fringe at this time versus each optical path length difference is assumed to be S(1), the light intensity I (k) detected in the interference light detecting means 40 is expressed by the following formula.

$$I(k) = \int_0^\infty S(l)[l + \cos(kl)]dl \qquad (1)$$

wherein k represents the wave number and 1 represents the optical path length difference. Formula (1) may be considered to be given as an interferogram of a light frequency range having a wave number of ω/c (k=ω/c) as a variable. Accordingly, a tomographic image is generated by obtaining in the image obtaining means 50 information on the distance of the object S from the measurement initiating position and information on the intensity of reflection by carrying out frequency analysis by Fourier-transform on the spectral interference fringes detected by the interference light detecting means 40 and determining the intensity S(1) of the interference light beam L4.

Operation of the optical tomography system 1 having a structure described above will be described with reference to FIGS. 1 and 2, hereinbelow. When a tomographic image is to be obtained, the optical path length is first adjusted by moving the movable stage 23 in the direction of the arrow A so that the object S is positioned in the measurable area. The laser beam L sweeping the wavelength at a period is subsequently emitted from the light source unit 10 and the laser beam L is divided into the measuring light beam L1 and the reference light beam L2 by the dividing means 3. The measuring light beam L1 is led by the optical probe 30 into a body cavity and is projected onto the object S. The reflected light beam L3 from the object S and the reference light beam L2 reflected by the reflecting mirror 22 are multiplexed, and the interference light beam L4 of the reflected light beam L3 and the reference light beam L2 is detected by the interference light detecting means 40. A tomographic image is obtained by carrying out frequency analysis on a signal of the detected interference light beam L4 in the image obtaining means 50.

The measurable range in the direction of depth of the object S where a tomographic image can be obtained by SS-OCT measurement depends on the wavelength fluctuation width, the wavelength fluctuation period or the like of the measuring light beam L1 and is limited to a predetermined range. When the probe 30 which is employed to obtain a tomographic image of the object S in the body cavity is changed, it is necessary to adjust the optical path length in order to compensate for the error in length of the optical fiber in the probe 30. Further, when the object S is remote from the probe 30, it is necessary to adjust the measurement initiating position so that the object S is in the measurable range. Accordingly, it is necessary to adjust the optical path length of the reference light beam L2 according to the distance between the probe 30 and the object S. When the measurement initiating position is adjusted, there is a problem that when the position of the reflecting mirror 22 is adjusted after detection and Fourier-analysis of the interference light L4 are effected, the distance between the probe 30 and the object S cannot be known until the end of the Fourier-analysis, which takes a long time to adjust the measurement initiating position.

Figure 3:
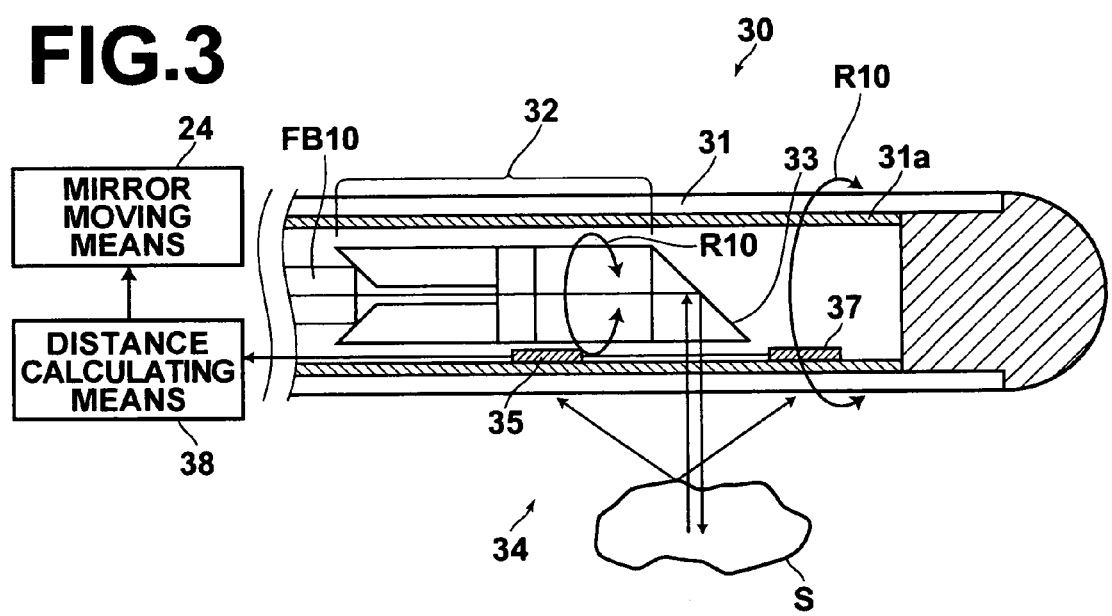
FIG. 3 is a schematic diagram showing a preferred example of the probe in the optical tomography system of FIG. 1.
Figure 4:
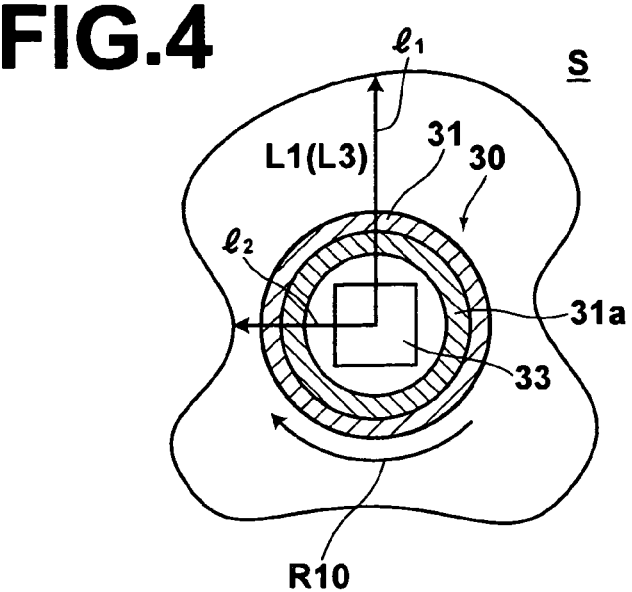
FIG. 4 is a schematic diagram showing another preferred example of the probe in the optical tomography system of FIG. 1.

In the optical tomography system 1, the probe 30 is provided with a distance measuring means 34 for measuring the distance to the object S. FIG. 3 is a schematic view of an example of the leading end portion of the probe 30 while FIG. 4 is a cross-sectional view of the same, and the probe 30 will be described with reference to FIGS. 3 and 4, hereinbelow. The probe 30 comprises an optical fiber FB30 which guides the measuring light L1 and the reflected light L3, a tube 31 which covers the optical fiber, and a light emitting portion 33 which emits the measuring light L1 propagated through the optical fiber FB30 to the object S. The tube 31 is formed by a flexible and light-transmitting material such as, for instance, a resin and a cap for sealing the tube 31 is fixed to the leading end of the tube 31.

An imaging optical system 32 such as a gradient index lens is provided on the leading end of the optical fiber FB30, and a light emitting portion 33 which may comprise a prism is fixed to an imaging optical system 32. The reference light L2 emitted from the optical fiber FB30 passes through the imaging optical system 32 and enters the light emitting portion 33. The light emitting portion 33 emits the propagated measuring light L1 toward the side wall of the tube 31 in the optical fiber FB30 and the measuring light L1 is projected onto the object S through the tube 31. The light emitting portion 33, at the same time, receives the reflected light L3 which is reflected by the object S when the measuring light L1 is projected onto the object S and emits it toward the optical fiber FB30.

The optical fiber FB30, the gradient index lens 32 and the light emitting portion 33 are integrally rotated with respect to the tube 31 in the direction of arrow R10 to cause the measuring light L1 emitted from the light emitting portion 33 to scan the object S while rotating in the direction of arrow R10. With this arrangement, optical tomographic image of the object S in a body cavity in the rotating direction (a radial direction) of the object S can be obtained.

Figure 5:
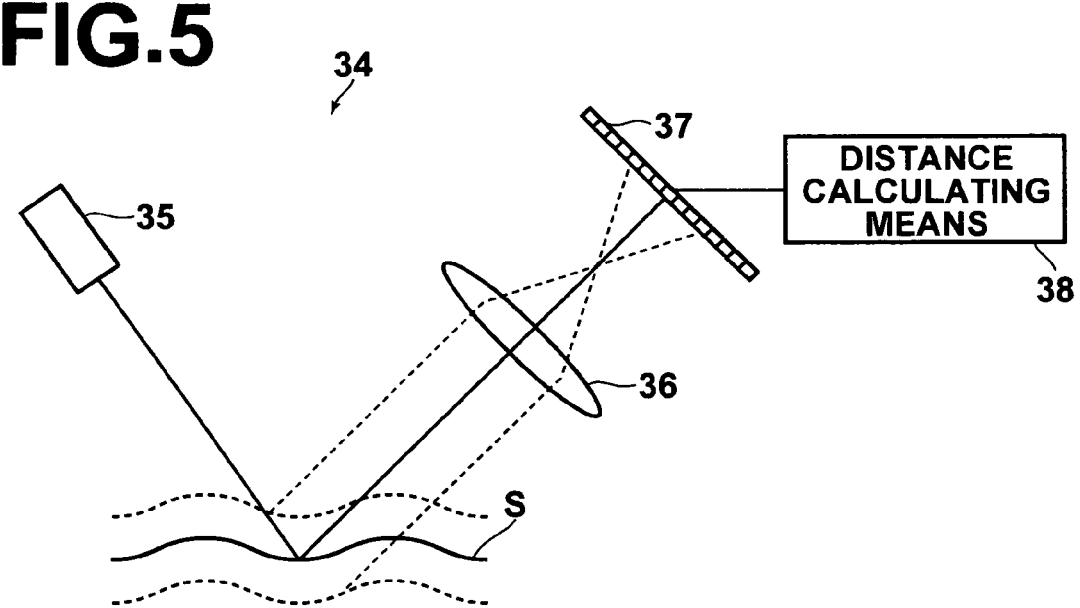
FIG. 5 is a schematic diagram showing a distance measuring means in the optical tomography system of FIG. 1, FIGS. 6A and 6B are views showing projection of the measuring light onto the object from the light emitting portion of FIG. 3, FIGS. 7A and 7B are schematic diagrams showing an example of the tomographic image obtained by the image obtaining means of FIG. 1.

The distance measuring means 34 has a housing 31a which is fixed to the inner surface of the tube 31 to be rotated in synchronization with the light emitting portion 33 and scans the object S to measure the distance to the measuring light projected part onto which the measuring light L1 emitted from the light emitting portion 33 is projected. The distance measuring means 34 comprises, as shown in FIG. 5, a measuring light source 35 which emits distance measuring light, an imaging lens 36 which images the reflected distance measuring light which is reflected at the surface of the object S when the distance measuring light emitted from the measuring light source 35 is projected onto the surface of the object S, a photo-sensor 37 which detects the reflected distance measuring light imaged by the imaging lens 36, and a distance calculating means 38 which calculates the distance to the object S from the detected position of the reflected distance measuring light by the photo-sensor 37.

The measuring light source 35 inputs the distance measuring light comprising a collimated light beam obliquely with respect to the object S and the reflected distance measuring light which is reflected at the object S is input into the imaging lens 36. The photo-sensor 37 detects the reflected distance measuring light imaged by the imaging lens 36 by the use of a one-dimensional or two-dimensional array sensor. At this time, the reflected distance measuring light is imaged on the photo-sensor 37 by the imaging lens 36 in positions different from each other according to the distance between the measuring light source 35 and the object S. The distance calculating means 38 measures the distance between the probe 30 and the object S by the use of trigonometry on the basis of the position of the measuring light source 35 and the detected position of the reflected distance measuring light by the photo-sensor 37. The mirror moving means 24 of the optical path length adjusting means 20 moves the reflecting mirror 22 in the direction of arrow A on the basis of the distance detected by the distance calculating means 38 (FIG. 1).

By thus effecting adjustment of the measurement initiating position on the basis of the result of measurement by the distance measuring means 34, the adjustment can be carried out in a shorter time than the conventional, where the adjustment is carried out on the basis of the result of frequency-analysis of the interference light L4. Further even if the distance between the probe 30 and the object S is larger than the measurable range, it is possible to measure the distance between the probe 30 and the object S. Accordingly, adjustment of the measurement initiating position or the position of the probe can be done more efficiently in a shorter time.

Figure 6A:
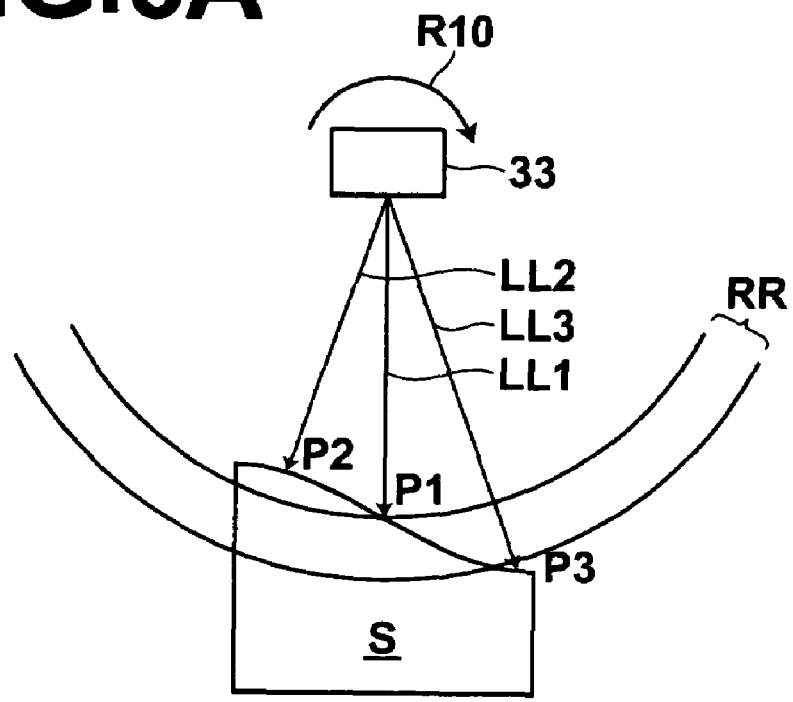

Further, when the light emitting portion 33 rotates in the direction of arrow R10 and the measuring light projected part is changed, the distances to the surfaces of the object S sometimes differ according to the parts onto which the measuring light L1 is to be projected. For example, it is assumed that the measurable range RR where a tomographic image can be obtained is annularly (having a radius of LL1) formed as shown in FIG. 6A in response to rotation of the light emitting portion 33 if adjustment of the optical path length by the optical path length adjusting means 20 is not carried out. In the measuring light projected part P1 where the distance to the surface of the object S is LL1, tomographic images from the surface of the object S to the measurable range RR can be obtained. Whereas, in the measuring light projected part P2 where the distance to the surface of the object S is LL2 (<LL1), the tomographic images cannot be obtained from the surface of the object S but the tomographic images can be obtained from inside the object S. Further, in the measuring light projected part P3 where the distance to the surface of the object S is LL3 (>LL1), the tomographic images cannot be obtained to a predetermined depth from the surface of the object S.

Figure 6B:
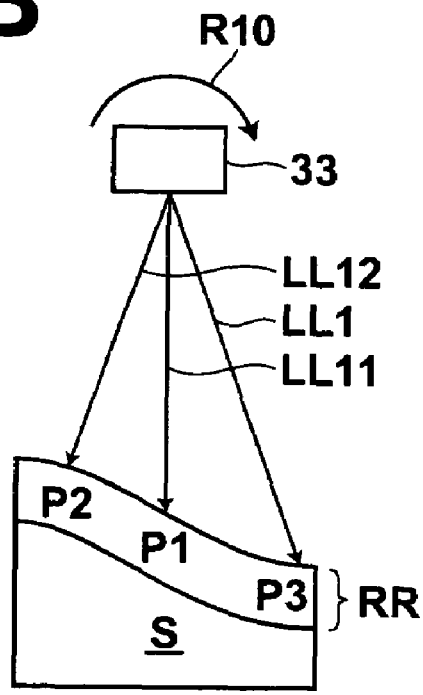

At this time, the optical path length is adjusted on the basis of the measurement by the distance measuring means 34 as shown in FIG. 6B. Specifically, in the case of the measuring light projected part P2, the optical path length of the reference light beam L2 is adjusted by the optical path length adjusting means 20 to be longer than in the measuring light projected part P1 so that the measurement initiating position falls in the surface of the object S. Whereas, in the case of the measuring light projected part P3, the optical path length of the reference light beam L2 is adjusted by the optical path length adjusting means 20 to be shorter than in the measuring light projected part P1 so that the measurement initiating position falls in the surface of the object S. Thus, for the measuring light projected parts p1 to p3 different from each other in the distance to the light emitting portion 33, tomographic images can be obtained from the same measurement initiating position (the surface of the object S) to the measurable range RR. Accordingly, obtainment of tomographic images of the unnecessary part is prevented and the tomographic images can be efficiently obtained.

Figure 7A:
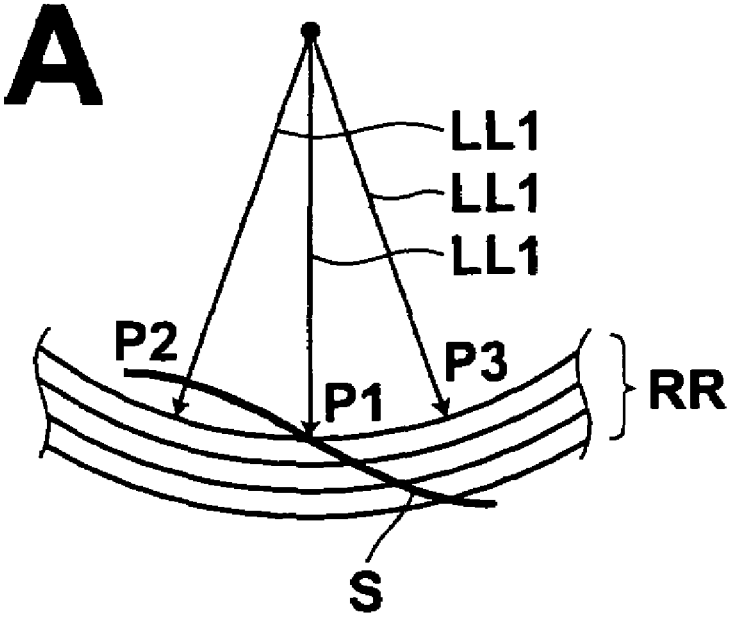
Figure 7B:
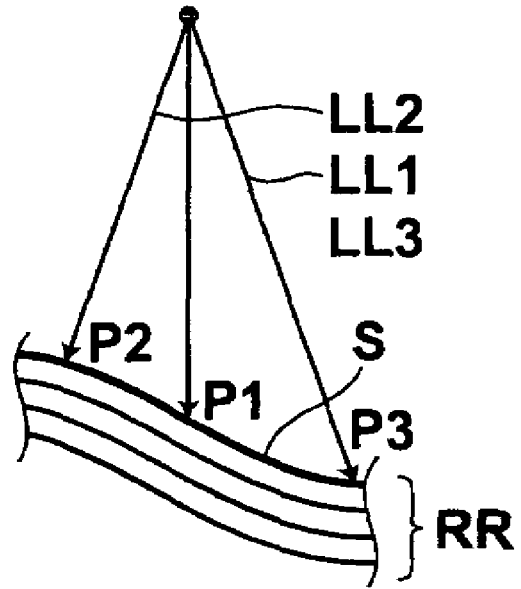

When though the optical path length has been adjusted on the basis of the measurement by the distance measuring means 34, the image obtaining means 50 neglects the adjustment, the measuring light projected parts p1 to p3 are respectively positioned in the measurement initiating position of the measurable range RR as shown in FIG. 7A, and tomographic images representing the actual shape of the object S cannot be obtained. Accordingly, as shown in FIG. 7B, the image obtaining means 50 corrects tomographic image on the basis of the adjustment of the optical path length based on the measurement by the distance measuring means 34. With this arrangement, tomographic images representing the actual shape of the object S can be obtained and at the same time, tomographic images of a depth from a predetermined reference plane (the surface of the object S) to the measurable range RR can be obtained. The image obtaining means 50 may employ either the adjustment of the optical path length or the distance measured by the distance measuring means 34 to correct the tomographic image.

FIG. 8 is a schematic view showing an optical tomography system of the present invention in accordance with another embodiment. The optical tomography system 100 will be described with reference to FIG. 8, hereinbelow. In the optical tomography system 100 of FIG. 8, the parts analogous to those in the optical tomography system 1 of FIG. 1 are given the same reference numerals and will not be described here.

The optical tomography system 100 of FIG. 8 differs from the optical tomography system 1 of FIG. 1 in the arrangement of the light source unit and the interference light detecting means. Specifically, the optical tomography system 100 obtains a tomographic image by a so-called SD-OCT measurement and the light source unit 110 comprises a light source 111 which emits low coherence light such as SLD (super luminescent diode) or ASE (amplified spontaneous emission) and an optical system 112 for entering the light emitted from the light source 111 into the optical fiber FB1. Since the optical tomography system 100 of this embodiment is for obtaining a tomographic image with a living tissue in a body cavity taken as the object S, it is preferred that the light source 111 be, for instance, a broad spectral band, ultra short pulse laser where attenuation of light due to scatter and/or absorption when transmitted through the object S is minimized.

The interference light detecting means 140 detects interference light L4 of the reflected light beam L3 and the reference light beam L2 which have been multiplexed by the multiplexing means 4, and comprises a spectral means 142 which divides the interference light beam L4 having a plurality of wavelength bands by the wavelength bands and a light detecting means 144 which detects the amount of light of each wavelength band of the interference light beam L4 divided by the spectral means 142. The spectral means 142 comprises, for instance, a diffraction grating element, and divides the interference light beam L4 entering it from an optical fiber FB4 by way of the collimator lens 141 to output the divided interference light beam L4 to the light detecting means 144.

The light detecting means 144 is formed by a plurality of photo sensors which comprises a plurality of, for instance, one-dimensionally or two-dimensionally arranged CCDs and each of the photo sensors detects each wavelength band of the interference light beam L4 entering by way of an optical system 143. In the light detecting means 144, the interference light L4 where the spectrum of the light source unit 110 is added with a Fourier-transformed function of information on the reflection is observed. Then, by carrying out frequency analysis in the image obtaining means 50 on the interference light beam L4 detected in the interference light detecting means 140, reflection information in the position of depth can be obtained.

Here, detection of the interference light beam L4 in the interference light detecting means 40 and image generation in the image obtaining means 50 will be described briefly. Note that a detailed description of these two points can be found in M. Takeda, "Optical Frequency Scanning Interference Microscopes", Optical Engineering Contact, Vol. 41, No. 7, pp. 426-432, 2003.

When the measuring light beam L1 having a spectral intensity distribution of S(k), the light intensity I(k) detected in the interference light detecting means 40 as the interferogram is expressed by the following formula.

$$I(l) = \int_0^\infty S(k)[l + \cos(kl)]dk \qquad (2)$$

wherein k represents the angular frequency and 1 represents the optical path length difference between the measuring light beam L1 and the reference light beam L2. Formula (2) expresses how much components of the angular frequency k of the interference fringe I(l) are included in the interference fringe I(I) where the spectral intensity distribution of each spectral component is S(k). Further, from the angular frequency k of the interference light fringes, the optical path length difference between the measuring light beam L1 and the reference light beam L2, that is, information on the position of depth, is given. Accordingly, S(k) of the interference light beam L4 can be obtained by carrying out frequency analysis by Fourier-transform on the interferogram detected by the interference light detecting means 40 in the image obtaining means 50. Then a tomographic image is generated by obtaining information on the distance of the object S from the measurement initiating position and information on the intensity of reflection. The generated tomographic image is displayed in the display 60.

Also in FIG. 8, the optical path length adjusting means 20 has a function of adjusting the optical path length of the reference light L2 in order to adjust the measurement initiating position. By moving the reflecting mirror 22 in the direction of arrow A on the basis of the distance to the object S measured by the distance measuring means 34, the measurement initiating position is adjusted. With this arrangement, the adjustment can be effected in a shorter time than the conventional, where the adjustment has been done on the basis of the interference light L4.

Figure 9:
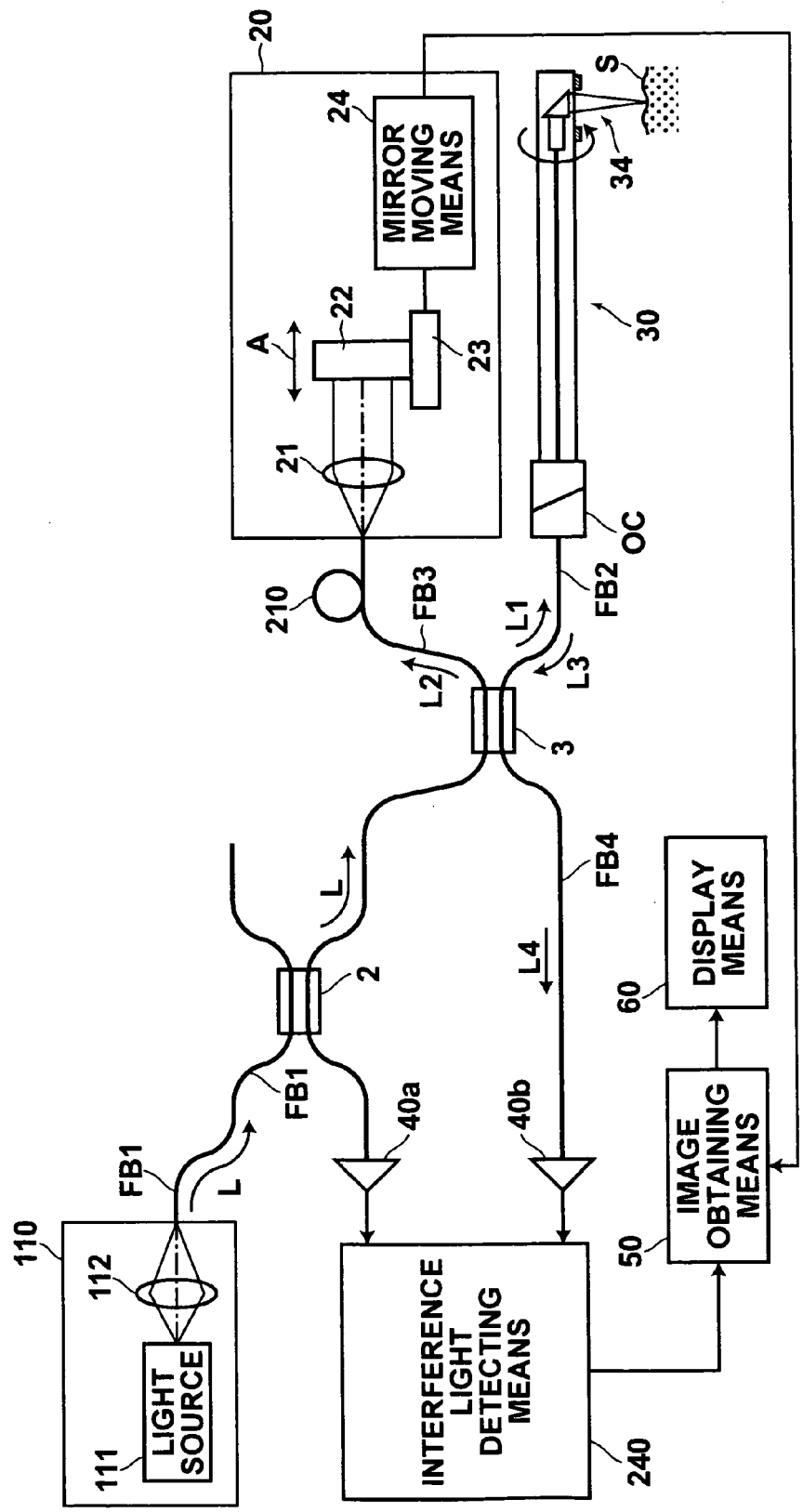
FIG. 9 is a schematic diagram showing an optical tomography system in accordance with a third embodiment of the present invention.

FIG. 9 is a schematic view showing an optical tomography system of the present invention in accordance with still another embodiment. The optical tomography system 200 will be described with reference to FIG. 9, hereinbelow. In the optical tomography system 200 of FIG. 9, the parts analogous to those in the optical tomography system 1 and 100 of FIGS. 1 and 5 are given the same reference numerals and will not be described here.

The optical tomography system 200 obtains a tomographic image by a so-called TD-OCT measurement and the optical path length adjusting means 20 has a function of changing the optical path length of the reference light L2 in order to change the measuring position in the object S. A phase modulator 210 is disposed on the optical path (optical fiber FB3) to give a slight frequency shift to the reference light L2. The reference light L2 which has been changed in its optical path length and shifted in its frequency by the optical path length adjusting means 20 is guided to the optical fiber FB4 or the multiplexing means 4.

Interference light detecting means 240 detects the intensity of the interference light L4 by, for instance, heterodyne detection. Specifically, when the sum of the total optical path length of the measuring light L1 and the total optical path length of the reflected light L3 is equal to the total optical path length of the reference light L2, a beat signal which varies in intensity at the difference frequency between the reference light L2 and the reflected light L3 is generated. As the optical path length is changed by the optical path length adjusting means 20, the measuring position (measuring depth) in the object S changes and the interference light detecting means 240 comes to detect beat signals in the measuring positions. On the basis of the beat signals detected by the interference light detecting means 240 and information on the measuring position in the mirror moving means 24, a tomographic image is generated.

Also in the optical tomographic system 200 where TD-OCT measurement is carried out, by providing the probe 30 with the distance measuring means 34, the adjustment of measurement initiating position can be more accurately effected in a shorter time than the conventional, where the search of the measurement initiating position has been done while the reflecting mirror is caused to scan.

In the embodiments described above, since the probe 30 is provided with the distance measuring means 34 and the optical path length of the reference light is adjusted by the use of the distance to the object S measured by the distance measuring means 34, the measurement initiating position when the tomographic image is obtained is set on the basis of the distance to the object measured not by the use of the interference light as in obtaining the tomographic image but measured by the distance measuring means, whereby the signal processing on the interference light to detect the measurement initiating position becomes unnecessary and the adjustment of the optical path length so that the object is included in the measurable range can be done in a short time.

Since the light emitting portion 33 of the probe 30 rotates to emit the measuring light beam L1 to the object S and the distance measuring means 34 rotates in synchronization with the light emitting portion 33, the distance measuring means 34 can measure the distance to the measuring light projected part of the object even if the distance to the measuring light projected part from the light emitting portion of the probe 30 is changed due to rotation of the light emitting portion 33, whereby the distance to the object S can be measured surely and accurately.

Further, when the distance measuring means 34 comprises a measuring light source 35 which emits distance measuring light toward the object S, a photo-sensor 37 which detects the reflected distance measuring light from the object S when the distance measuring light is projected onto the object S from the measuring light source 35, and a distance calculating means 38 which calculates the distance to the object S from the reflected distance measuring light detected by the photo-sensor 37 as shown in FIG. 3, the distance to the object S can be accurately measured at high speed.

The distance measuring means 34 described above may be applied to any one of the optical tomography systems 1 (FIG. 1:SS-OCT), 100 (FIG. 5:SD-OCT) and 200 (FIG. 6:TD-OCT).

The present invention is not limited to the above embodiments. For example, though the distance measuring means 34 shown in FIGS. 3 and 4 measures the distance by the use of trigonometry, by way of example, the distance may be measured in a short distance by any one of known technics such as by the ultrasonic waves, by the sharpness of a CCD image imaged by a lens or by an optical distance measuring method so long as the system can be compactly accommodated.

Further, though, in FIGS. 1, 8 and 9, the optical path length adjusting means 20 adjusts the optical path length of the reference light L2, by way of example, the optical path length adjusting means 20 may adjust the optical path length of the measuring light L1. In this case, for example, a three-way optical circulator is provided in the optical fiber FB2 which guides the measuring light L1 and the optical path length adjusting means 20 is interposed in a vacant port. The return light from the object S is led to the optical path length adjusting means 20, and the reflected light from the reflecting mirror 22 at the terminal end of the optical path length adjusting means 20 is returned to the multiplexing means 4.

Further, though, the interference light beam L4 is detected as a beat signal in FIG. 9, the interference light beam L4 may be detected as an interferogram by not providing the phase modulating means 210 in the optical path of the reference light beam L2 (e.g., the optical fiber FB3) as shown in FIG. 3.

What is claimed is:

1. An optical tomography system for obtaining a tomographic image of an object to be measured comprising
    a light source unit which emits light,
    a light dividing means which divides the light emitted from the light source unit into measuring light and reference light,
    an optical path length adjusting means which adjusts the optical path length of the measuring light or the reference light divided by the light dividing means,
    a probe having an optical fiber which guides to the object the measuring light divided by the light dividing means and a light emitting portion which emits from an optical fiber the measuring light scanning the object,
    a multiplexing means which multiplexes the reflected light from the object when the measuring light emitted from the probe is projected onto the object and the reference light,
    an interference light detecting means which detects interference light of the reflected light and the reference light which have been multiplexed by the multiplexing means, and
    a tomographic image obtaining means which obtains a tomographic image of the object on the basis of the interference light detected by the interference light detecting means,
    the probe being provided with a distance measuring means which measures the distance to the measuring light projected part onto which the measuring light emitted from the light emitting portion is projected,
    the distance measuring means comprising:
        a measuring light source which emits distance measuring light,
        a photo-sensor which detects distance measuring light reflected from the object,
        an imaging lens which forms an image of the object, with distance measuring light, on a photo-sensor at a position which varies according to a distance between the measuring light source and the object, and
        a distance calculating means which calculates a distance to the object based on a position of the measuring light source and a detected position of the distance measuring light incident on the photo-sensor; and
    the optical path length adjusting means adjusting the optical path length of the measuring light or the reference light by the use of the distance to the object measured by the distance measuring means in order to adjust the position in which a tomographic image signal is to be obtained in synchronization with scanning of the measuring light.

2. An optical tomography system as defined in claim 1 in which the tomographic image obtaining means has a function of correcting the distance between the probe and the measuring light projected part in the tomographic image on the basis of the distance between the probe and the measuring light projected part of the object measured by the distance measuring means when the measuring light is projected onto the object while scanning the object.

3. An optical tomography system as defined in claim 1 in which the light source unit emits a laser beam while sweeping the wavelength, while the image obtaining means obtains a tomographic image of the object by carrying out frequency-analysis on the interference light, and the optical path length adjusting means adjusts the optical path length of the measuring light or the reference light in order to adjust the position in which a tomographic image signal is to be obtained.

4. An optical tomography system as defined in claim 1 in which the light source unit emits low coherence light while the image obtaining means obtains a tomographic image of the object by carrying out frequency-analysis on the interference light, and the optical path length adjusting means adjusts the optical path length of the measuring light or the reference light in order to adjust the position in which a tomographic image signal is to be obtained.

5. An optical tomography system as defined in claim 1, wherein the distance measuring means comprises at least one photo-sensor disposed in the probe.

6. An optical tomography system as defined in claim 1, wherein the measuring light source and the photo-sensor are disposed laterally on a surface of the probe, such that the photo-sensor receives distance measuring light reflected by the object.

* * * * *